United States Patent
Lange et al.

(10) Patent No.: US 7,563,856 B2
(45) Date of Patent: *Jul. 21, 2009

(54) LINEAR POLYAMINO AND/OR POLYAMMONIUM POLYSILOXANE COPOLYMERS II

(75) Inventors: Horst Lange, Bochum (DE); Anita Witossek, Langenfeld (DE); Roland Wagner, Bonn (DE); Karl-Heinz Stachulla, Leverkusen (DE); Andrew Russell Graydon, Tyne and Wear (GB); Richard Timothy Hartshorn, Cincinnati, OH (US); Jean Pol Boutique, Gembloux (BE); Patrick Firmin August Delplanque, Laarne (BE); James Pyott Johnston, Merchtem (BE); Karl-Heinz Sockel, Leverkusen (DE)

(73) Assignee: Momentive Performance Materials GmbH, Leverkusen (DE)

( * ) Notice: Subject to any disclaimer, the term of this patent is extended or adjusted under 35 U.S.C. 154(b) by 346 days.

This patent is subject to a terminal disclaimer.

(21) Appl. No.: 10/533,837

(22) PCT Filed: Oct. 31, 2003

(86) PCT No.: PCT/EP03/50773

§ 371 (c)(1),
(2), (4) Date: Mar. 20, 2006

(87) PCT Pub. No.: WO2004/042136

PCT Pub. Date: May 21, 2004

(65) Prior Publication Data

US 2006/0235181 A1    Oct. 19, 2006

(30) Foreign Application Priority Data

Nov. 4, 2002    (DE) ............... 102 51 524

(51) Int. Cl.
*C08G 77/54* (2006.01)
(52) U.S. Cl. .......... 528/25; 528/28; 252/8.61; 252/8.63
(58) Field of Classification Search ............ None
See application file for complete search history.

(56) References Cited

U.S. PATENT DOCUMENTS

| 4,833,225 | A | 5/1989 | Schaefer et al. | |
| 5,807,956 | A | 9/1998 | Czech | |
| 6,818,610 | B2 * | 11/2004 | Zhang et al. | 510/516 |
| 7,041,767 | B2 * | 5/2006 | Lange et al. | 528/28 |
| 7,217,777 | B2 * | 5/2007 | Lange et al. | 528/28 |

FOREIGN PATENT DOCUMENTS

| DE | 10036699 A1 | | 2/2002 |
| DE | 102004002208 | * | 8/2005 |
| WO | 02/10256 A1 | | 2/2002 |
| WO | 02/10259 A1 | | 2/2002 |

OTHER PUBLICATIONS

International Search Report for PCT/EP03/50773 mailed Apr. 2, 2004, three pages.

* cited by examiner

*Primary Examiner*—Marc S Zimmer
(74) *Attorney, Agent, or Firm*—Rankin, Hill & Clark LLP

(57) ABSTRACT

The invention relates to linear polyamino- and/or polyammonium-polysiloxane copolymers, particularly hydrophilic polyquaternary polysiloxane copolymers, and to their use in cosmetic formulations, in laundry detergents or for surface-treating substrates.

14 Claims, No Drawings

LINEAR POLYAMINO AND/OR POLYAMMONIUM POLYSILOXANE COPOLYMERS II

The invention relates to linear polyamino- and/or polyammonium-polysiloxane copolymers, particularly hydrophilic polyquaternary polysiloxane copolymers, and to their use as wash-stable hydrophilic softeners.

Polysiloxanes containing amino groups are known for use as textile softeners (EP 441530). The introduction as side chains of amino structures modified by ethylene oxide/propylene oxide units produces an improvement in the effect (U.S. Pat. Nos. 5,591,880, 5,650,529). The alkylene oxide units here allow controlled adjustment of the hydrophilic/hydrophobic balance. Disadvantages are, from the synthetic standpoint, the difficulty of the esterification that is included in the synthesis strategy, namely that of amino alcohols with siloxane-bonded carboxylic acid groups, and, in respect of the softening properties, the general comb structure of the products.

To eliminate these disadvantages proposals have been made to react α,ω-epoxy-modified siloxanes with α,ω-amino-functionalized alkylene oxides, and to use these products as hydrophilic softeners (U.S. Pat. Nos. 5,807,956, 5,981,681).

In order to improve the substantivity, experiments have been undertaken on introducing quaternary ammonium groups into alkylene oxide-modified siloxanes.

Branched, alkylene oxide-modified polysiloxane quats ("polysiloxane quats" are polydiorganosiloxane-polyalkylammonium compounds) have been synthesized from α,ω-OH-terminated polysiloxanes and trialkoxysilanes by condensation. The quaternary ammonium structure is introduced via the silane, with the quaternary nitrogen atom being substituted by alkylene oxide units (U.S. Pat. No. 5,602,224).

Strictly comblike alkylene oxide-modified polysiloxanequats have likewise been described (U.S. Pat. No. 5,098,979). The hydroxyl groups of polyethersiloxanes with comblike substitution are converted with epichlorohydrin into the corresponding chlorohydrin derivatives. That is followed by quaternization with tertiary amines. For this reason the hydroxyl groups of polyethersiloxanes with comblike substitution have alternatively been esterified with chloroacetic acid. The carbonyl activation allows the final quaternization to be completed more easily (U.S. Pat. Nos. 5,153,294, 5,166,297).

U.S. Pat. No. 6,242,554 describes α,ω-difunctional siloxane derivatives which each possess a separate quaternary ammonium and alkylene oxide unit. These materials are distinguished by an enhanced compatibility with polar environments.

The reaction of α,ω-diepoxides with tertiary amines in the presence of acids yields α,ω-diquaternary siloxanes, which can be used for haircare purposes (German Patent Specification 37 19 086). Besides tetraalkyl-substituted quaternary ammonium structures, aromatic imidazolinium derivatives as well are claimed.

Reducing the ease with which the compounds are washed out of hair can be achieved by reacting the α,ω-diepoxides with ditertiary amines in the presence of acids to give long-chain polyquaternary polysiloxanes (EP 282720). Aromtic quaternary ammonium structures are not disclosed. Derivatives of this kind are addressed in U.S. Pat. No. 6,240,929. In a first step, for this purpose, diamines having two imidazole units are synthesized from imidazole and suitable difunctional alkylating agents, and these diamines are subsequently converted, in a manner analogous to that of EP 282720, into polyquaternary polysiloxanes. Cationic compounds prepared in this way are said to possess a further-increased compatibility with the anionic surfactants that are present in cosmetic formulations.

Nevertheless, the stability with respect to being washed out of hair relates to the short-term attack of, principally, water and very mild, non-skin-irritant surfactants, whereas wash-stable hydrophilic softeners for textiles have to resist the attack of concentrated surfactant solutions possessing high fat and soil solvency. A further complicating factor is that modern laundry detergents contain strongly alkaline complexing agents, oxidative bleaches, and complex enzyme systems, and the fibers are exposed to their effects often for hours at elevated temperatures.

WO 02/10259 discloses polyquaternary polysiloxane compounds incorporated in which additionally are hydrophilic units (EO units), and in which the arrangement and sequence of the quat units to hydrophilic units can be modified such that it is subsequently possible to achieve a better hydrophilic soft hand without loss of substantivity on, for example, textiles (cotton, polyester).

Further approaches at improving the compatibility with anionic surfactant systems and/or the efficiency of siloxane deposition on surfaces are directed at the use of relatively large amounts of cationic surfactants (WO 00/71806 and WO 00/71807) or at the utilization of cationic polysaccharide derivatives (J. V. Gruber et al., Colloids and Surfaces B: Biointerfaces 19 (2000) 127-135) in mixtures with polydimethylsiloxanes.

Highly charged, very hydrophilic synthetic polycationics are likewise capable of improving the compatibility with anionic surfactant systems (U.S. Pat. No. 6,211,139), or of associating with fibers in the presence of solutions of anionic surfactants (WO 99/14300). Among the compounds described in the latter publication are polyimidazolinium derivatives.

None of the proposals addressed constitutes a satisfactory solution to the problem of obtaining the silicone-mediated soft hand and the pronounced hydrophilicity following original finishing of a textile material even when said material is subject to the attack of aggressive detergent formulations in the course of repeated laundering operations at normal or elevated temperature.

A fundamentally different approach is described in DE-A 32 36,466. The reaction of OH-terminated siloxanes with alkoxy silanes containing quaternary ammonium structures yields reactive intermediates which are said to crosslink with suitable crosslinking agents, such as trialkoxysilanes, on the fiber surface to form wash-stable layers. A decisive disadvantage of this approach is that the hours-long stability required of an aqueous finishing bath cannot be guaranteed and that unforeseen crosslinking reactions may occur in the bath even before textile finishing.

WO 02/10257 discloses polysiloxane compounds containing quaternary ammonium groups and synthesized from diamines, diepoxides containing polydiorganosiloxane groups, and di(haloalkyl) ester polyether compounds. As an inevitable result of their preparation, however, these polysiloxane compounds include a certain fraction of ester groups, which specifically are sensitive to hydrolysis under alkaline conditions, as a key constituent. Moreover, in the polysiloxane compounds described therein, the ratio between softening polydiorganosiloxane blocks and hydrophilic blocks is rigid. The properties of these polysiloxane compounds can-not, therefore, always be tailored to particular requirements. for instance, for certain applications, the hydrophilicity of these polysiloxane compounds is not always satisfactory, while in other applications the soft hand or the substantivity leaves something to be desired.

None of the solutions cited teaches how it is possible to achieve a further increase in hydrophilicity and substantivity while retaining the soft hand, or how, in particular, these properties can, so to speak, be tailored for specific applications.

It is therefore an object of the invention to provide linear polysiloxane copolymers, their preparation, and their use as wash-stable hydrophilic softeners, the linear polysiloxane copolymers endowing the textiles after corresponding application with a soft hand typical for silicones and with a pronounced hydrophilicity, with this pattern of properties not being lost even after exposure to detergent formulations in the course of repeated laundering operations at normal or elevated temperature. It is a further object of the invention to provide for the use of these linear polysiloxane copolymers as separate softeners after the laundering of fibers and/or textiles, and as softeners in laundering with formulations based on nonionic or on anionic/nonionic surfactants. Additionally the linear polysiloxane copolymers ought to prevent or reduce textile creasing. A final object of the present invention is to provide a linear polysiloxane copolymer whose properties in respect of soft hand, substantivity, hydrophilicity or the like can be easily tailored to a respective application.

The present invention accordingly provides linear polyamino- and polyammonium-polysiloxane copolymers containing the repeating unit

-[Q-V-]- (I)

in which Q is selected from the group consisting of
—NR—,
—N$^+$R$_2$—,
a saturated or unsaturated diamino-functional heterocycle of the formulae

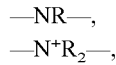

an aromatic diaminofunctional heterocycle of the formula

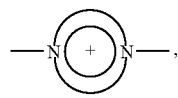

a trivalent radical of the formula:

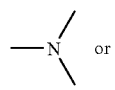

a trivalent radical of the formula

in which R in each case is hydrogen or a monovalent organic radical,

Q not bonding to a carbonyl carbon atom,

V represents at least one group V$^1$ and at least one group V$^2$ in which

V$^2$ is selected from divalent or trivalent, straight-chain, cyclic or branched, saturated, unsaturated or aromatic hydrocarbon radicals having up to 1000 carbon atoms (not including the carbon atoms of the polysiloxane radical Z$^2$, defined below) and containing, if desired, one or more groups selected from
—O—, —CONH—,
—CONR$^2$—, in which R$^2$ is hydrogen, a monovalent, straight-chain, cyclic or branched, saturated, unsaturated or aromatic hydrocarbon radical having up to 100 carbon atoms, which may contain one or more groups selected from —O—, —NH—, —C(O)— and —C(S)—, and which may if desired be substituted by one or more substituents selected from the group consisting of a hydroxyl group, an unsubstituted or substituted heterocyclic group preferably containing one or more nitrogen atoms, amino, alkylamino, dialkylamino, ammonium, polyether radicals and polyetherester radicals, and, if there are two or more groups —CONR$^2$—, they may be identical or different,
—C(O)— and —C(S)—, and
the radical V$^2$ may if desired by substituted by one or more hydroxyl groups, and the radical V$^2$ contains at least one group -Z$^2$- of the formula

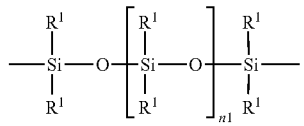

in which

R$^1$ can be identical or different and is selected from the group consisting of C$_1$ to C$_{22}$ alkyl, fluoro(C$_1$-C$_{10}$)alkyl and C$_6$-C$_{10}$ aryl, and n$_1$=20 to 1000, V$^1$ is selected from dihydric or trihydric, straight-chain, cyclic or branched, saturated, unsaturated or aromatic hydrocarbon radicals having up to 1000 carbon atoms, which if desired may contain one or more groups selected from
—O—, —CONH—,
—CONR$^2$—, in which R$^2$ is as defined above, it being possible for the groups R$^2$ in the groups V$^1$ and V$^2$ to be identical or different,
—C(O)—, —C(S)— and -Z$^1$-, in which -Z$^1$- is a group of the formula

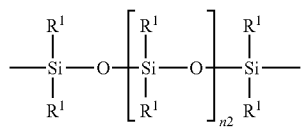

in which
- $R^1$ is as defined above, it being possible for the groups $R^1$ in the groups $V^1$ and $V^2$ to be identical or different, and
- $n_2=0$ to 19,
- and the radical $V^1$ may if desired be substituted by one or more hydroxyl groups, with the provisos
that the radical $V^1$ may not contain any ester group(s) —C(O)—O— and/or —O—C(O)—,
that the trivalent radicals Q and the trivalent radicals $V^1$ or $V^2$ serve exclusively for saturating one another within the linear main chain of the stated polysiloxane copolymers, and
that in the stated polysiloxane copolymer the molar ratio $V^2/V^1 \neq 1$, and in which the positive charges resulting from the ammonium groups are neutralized by organic or inorganic acid anions,
and the acid addition salts thereof.

In one preferred embodiment of the invention Q is selected from the group consisting of
- —NR—,
- —N⁺R²—,
- a saturated or unsaturated diamino-functional heterocycle of the formulae

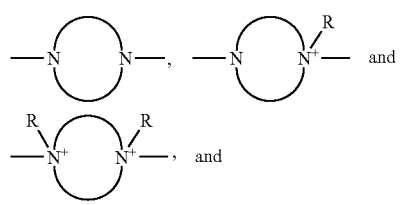

an aromatic diamino-functional heterocycle of the formula

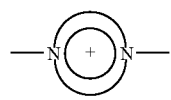

in which R is as defined above, and $V^1$ and $V^2$ are divalent radicals.

In one preferred embodiment of the invention Q is selected from the group consisting of
an amino unit of the formula

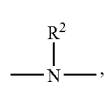

an ammonium unit of the formula

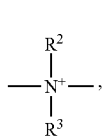

a quaternized imidazole unit of the structure

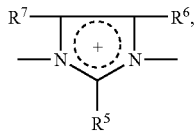

a quaternized pyrazole unit of the structure

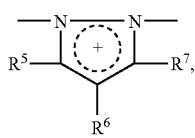

a diquaternized piperazine unit of the structure

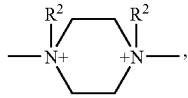

a monoquaternized piperazine unit of the structure

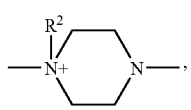

a monoquaternized piperazine unit of the structure

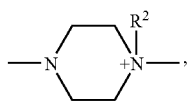

a diquaternized unit of the structure

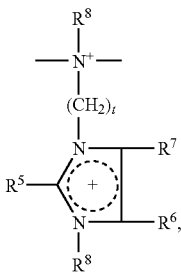

a monoquaternized unit of the structure

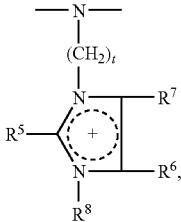

a monoquaternized unit of the structure

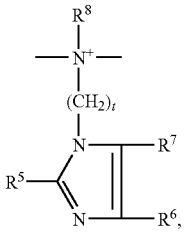

a diquaternized unit of the structure

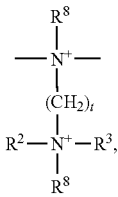

a monoquaternized unit of the structure

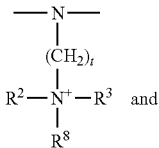 and a monoquaternized unit of the structure

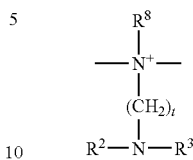

in which
t is from 2 to 10,
$R^2$ is as defined above, and the definition of $R^2$ may be identical to or different from the definition of the above group $R^2$,
$R^3$ has the definition of $R^2$, it being possible for $R^2$ and $R^3$ to be identical or different, or
$R^2$ and $R^3$ together with the positively charged nitrogen atom form a five- to seven-membered heterocycle, which if desired may additionally contain one or more nitrogen, oxygen and/or sulfur atoms,
$R^5$, $R^6$ and $R^7$ can be identical or different and are selected from the group consisting of H, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the type —$NHR^W$, in which $R^W$ is H, alkyl group, monohydroxyalkyl group, polyhydroxyalkyl group, acetyl group or ureido group, and pairs of adjacent radicals $R^5$, $R^6$ and $R^7$ may, with the carbon atoms bonding them to the heterocycle, form aromatic five- to seven-membered rings, and
$R^8$ has the definition of $R^2$, it being possible for $R^8$ and $R^2$ to be identical or different.
In a further preferred embodiment of the present invention $V^2$ is a group of the formula $$-V^{2*}-Z^2-V^{2*}-$$

in which $Z^2$ is as defined above and $V^{2*}$ is a divalent straight-chain cyclic or branched, saturated, unsaturated or aromatic hydrocarbon radical having up to 40 carbon atoms, which if desired may contain one or more groups selected from —O—, —CONH—, —$CONR^2$—, in which $R^2$ is as defined above, —C(O)— and —C(S)—, and the radical $V^{2*}$ may if desired be substituted by one or more hydroxyl groups.
Preferably also $V^2$ and/or $V^{2*}$ contains no ester groupings —C(O)—O— and/or —O—C(O)—.
Where Q is a trivalent radical of the formula

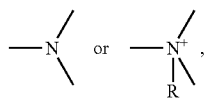

these radicals do not serve for the branching of the polysiloxane copolymers; instead, these radicals are joined exclusively to trivalent radicals $V^1$ or $V^2$, forming cyclic structures which are a constituent of the linear main chain, such as, for example, a structural element of the formula

Likewise the trivalent radicals $V^1$ and/or $V^2$ do not serve for the branching of the linear polysiloxane copolymers.

In the abovementioned embodiment the linear polysiloxane copolymer of the invention contains the following repeating units:

-[$V^{2*}$-$Z^2$-$V^{2*}$-Q]- and -[$V^1$-Q]-.

The molar ratio of the repeating units -[$V^{2*}$-$Z^2$-$V^{2*}$-Q]- to -[$V^1$-Q]- corresponds to the ratio $V^2/V^1 \neq 1$.

On the basis of these molar ratios the linear polysiloxane copolymers of the invention necessarily include blocks which contain more than one -[$V^1$-Q]- unit and/or -[$V^2$-Q]- unit linked to one another.

As elucidated in greater depth below in connection with the process of the invention for preparing the linear polysiloxane copolymers of the invention, the blocklike sequences which contain more than one -[$V^1$-Q]- unit linked to one another, and thus in which $V^2/V^1$ is <1, are joined, depending on mode of preparation, regularly to the $V^2$-Q- units or irregularly to the $V^2$-Q- units.

The meaning of this is as follows:

in the case of regular joining, where, for example, a prepolymer corresponding to the group -Q-[$V^1$-Q]$_x$- is reacted with monomer units corresponding to $V^2$ in a molar ratio of 1:1, the linear polysiloxane copolymers may be represented as follows:

-{$V^2$-Q-[$V^1$-Q]$_x$-}-.

x here may preferably be 1.01 to 2000 and is the average value. The linear polysiloxane copolymers represented with the formula -{$V^2$-Q-[$V^1$-Q]$_x$-}- are characterized in that they contain substantially no interlinked -$V^2$-Q- units, or, in other words, two -$V^2$-Q- units are always interrupted by at least one -$V^1$-Q- unit.

If $V^2/V^1$ is >1, then x in the above formula is preferably approximately 0.001 to 0.99. In this case the linear polysiloxane copolymers contain at least one interlinked -$V^2$-Q- unit, or, in other words, two $V^1$-Q- units are always interrupted by at least one $V^2$-Q- unit.

In the case of the irregular joining, in which, for example, monomers corresponding to Q units are reacted with monomer units corresponding to $V^1$ and monomer units corresponding to $V^2$ in a ratio Q/($V^1$+$V^2$), where $V^2/V^1 \neq 1$, of 1:1, the linear polysiloxane copolymers may be represented as follows:

-Q-($V^1$,$V^2$)-, in which the ratio $V^2/V^1 \neq 1$. In this case the groups $V^1$ and $V^2$ are distributed randomly over the copolymer chain. In contradistinction to the linear polysiloxane copolymers prepared by the regular joining, this copolymer may also contain adjacent -Q-$V^2$- and/or -Q-$V^1$- units.

In a further preferred embodiment of the present invention the group $V^1$ is selected from divalent, straight-chain, cyclic or branched, saturated, unsaturated or aromatic hydrocarbon radicals having up to 400 carbon atoms, which may if desired contain one or more groups selected from —O—, —CONH—, —CONR$^2$—, in which R$^2$ is as defined above, —C(O)—, —C(S)— and -$Z^1$-, in which -$Z^1$- is a group of the formula

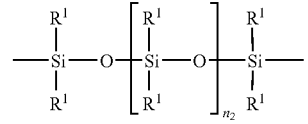

in which $R^1$ is $C_1$ to $C_3$ alkyl, fluoro($C_3$-$C_6$)alkyl or $C_6$ aryl, and $n_2$ is as defined above.

In a further preferred embodiment of the present invention the group Q is selected from:

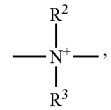

a quaternized imidazole unit of the structure

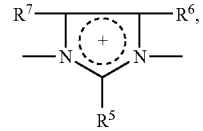

a quaternized pyrazole unit of the structure

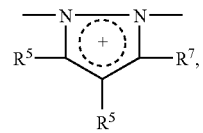

a diquaternized piperazine unit of the structure

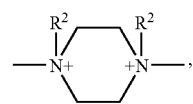

a monoquaternized piperazine unit of the structure

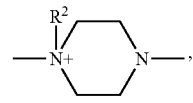

a monoquaternized piperazine unit of the structure

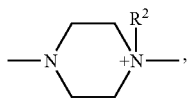

a monoquaternized unit of the structure

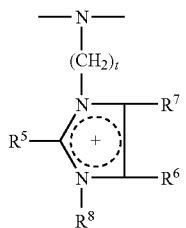

in which $R^2$, $R^3$, $R^4$, $R^5$, $R^6$, $R^7$ and $R^8$ are as defined above.

In a further preferred embodiment of the present invention, particularly in applications where increased hydrophilicity of the linear polysiloxane copolymers of the invention is a priority, the molar ratio $V^2/V^1$ complies with the relationship $V^2/V^1<1$, more preferably with the relationship $0.0005<V^2/V^1<0.9$, more preferably still with the relationship $0.005<V^2/V^1<0.8$, more preferably still with the relationship $0.01<V^2/V^1<0.5$.

In a further preferred embodiment of the present invention, especially in applications where an increased soft hand with consistent substantivity of the linear polysiloxane copolymers of the invention is a priority, such as in the case of certain textile finishes, for example, the molar ratio $V^2/V^1$ preferably complies with the relationship $V^2/V^1>1$, more preferably with the relationship $1<V^2/V^1<1000$, more preferably still with the relationship $1.1<V^2/V^1<100$, more preferably still with the relationship $2<V^2/V^1<20$.

With preference:

$R^1$=$C_1$ to $C_{18}$ alkyl, especially methyl, ethyl, perfluoroalkylethylene, such as trifluoropropyl, and phenyl, $n_1$=20 to 400, more preferably 20 to 300, especially 20 to 200. In a further preferred embodiment $n_1$ is between 20 and 50 or between 80 and 200. The number $n_1$ is the average degree of polymerization of the diorganosiloxy units in the group $Z^2$.

$n_2$=0 to 15, more preferably 0 to 10, especially 0 to 5, more especially 0. The number $n_2$ is the average degree of polymerization from Mn of the diorganosiloxy units in the group $Z^1$.

$V^{2*}$=a divalent straight-chain, cyclic or branched, saturated, unsaturated $C_3$ to $C_{16}$ hydrocarbon radical or aromatic $C_8$ to $C_{20}$ hydrocarbon radical which if desired may contain one or more groups selected from —O—, —CONH—, —CONR$^2$—, —C(O)— and —C(S)— and may be substituted by one or more than one OH group, in which $R^2$=hydrogen, a monovalent straight-chain, cyclic or branched, saturated, unsaturated $C_1$ to $C_{16}$ hydrocarbon radical or aromatic $C_6$ to $C_{16}$ hydrocarbon radical which may contain one or more groups selected from —O—, —NH—, —C(O)— and —C(S)— and which may if desired be substituted by one or more than one hydroxyl group, and, if there are two or more groups —NR$^2$, they may be identical or different,

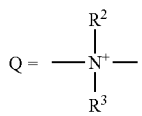

a quaternized imidazole unit of the structure

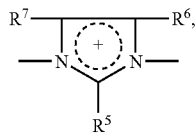

a diquaternized piperazine unit of the structure

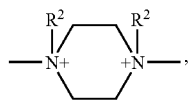

a monoquaternized piperazine unit of the structure

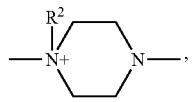

a monoquaternized piperazine unit of the structure

a monoquaternized unit of the structure

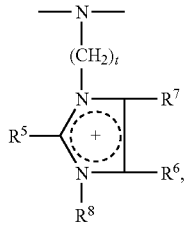

in which $R^2$, $R^3$, $R^4$, $R^5$, $R^6$, $R^7$ and $R^8$ are as defined above.

With particular preference $V^{2*}$ is a divalent straight-chain, cyclic or branched, saturated, unsaturated or aromatic hydrocarbon radical having up to 16 carbon atoms, which may contain one or more groups selected from —O—, —CONH—, —CONR$^2$—, in which $R^2$ is as defined above, —C(O)— and —C(S)—, and may be substituted by one or more hydroxyl groups. More preferably still -$V^{2*}$- is selected from groups of the following formulae:

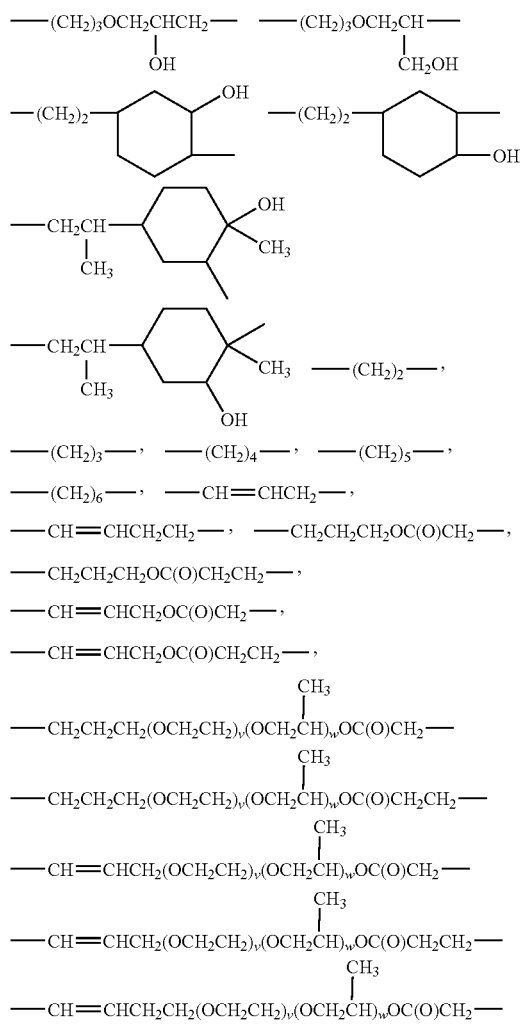

—CH=CHCH$_2$CH$_2$(OCH$_2$CH$_2$)$_v$(OCH$_2$CH)$_w$OC(O)CH$_2$CH$_2$—  | CH$_3$

—(CH$_2$)$_{10}$C(O)(OCH$_2$CH$_2$)$_v$(OCH$_2$CH)$_w$OC(O)CH$_2$CH$_2$—  | CH$_3$

—(CH$_2$)$_{10}$C(O)(OCH$_2$CH$_2$)$_v$(OCH$_2$CH)$_w$OC(O)CH$_2$—  | CH$_3$ with v + w > 0,    —(CH$_2$)$_3$OCH$_2$CHCH$_2$—  | OH

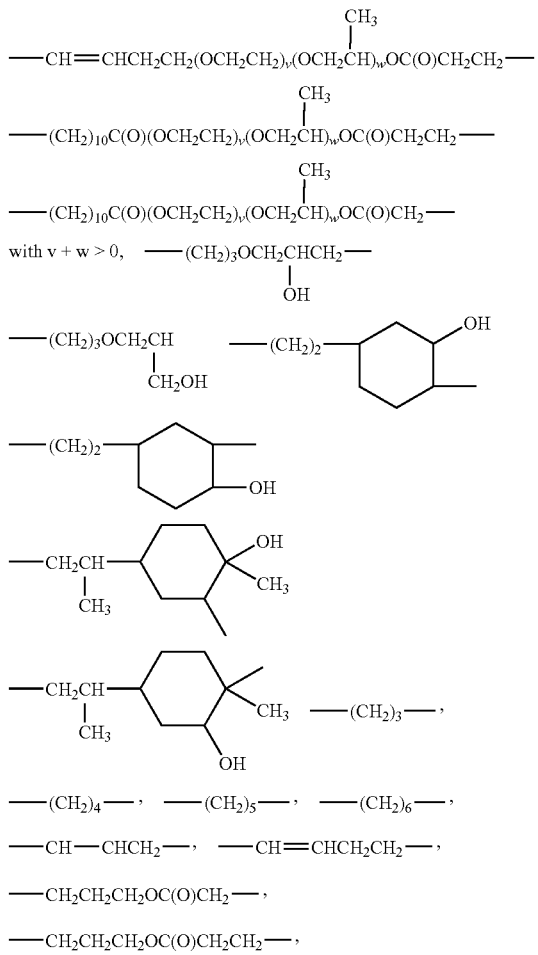

$R^2$ is preferably:

hydrogen,  —CH$_3$,  —CH$_2$CH$_3$,  —(CH$_2$)$_2$CH$_3$, —(CH$_2$)$_3$CH$_3$, —(CH$_2$)$_5$CH$_3$, —CH$_2$CH$_2$OH,

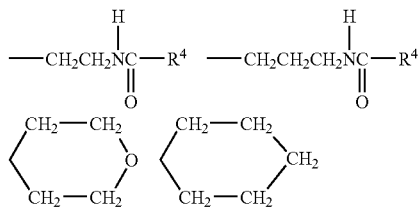

with $R^4$=straight-chain, cyclic or branched $C_1$ to $C_{18}$ hydrocarbon radical which may contain by one or more groups selected from —O—, —NH—, —C(O)—, and —C(S)— and may be substituted by one or more OH groups, especially unsubstituted $C_5$ to $C_{17}$ hydrocarbon radicals which are derived from the corresponding fatty acids or else hydroxylated $C_3$ to $C_{17}$ radicals which can be traced back to hydroxylated carboxylic acids, especially saccharide carboxylic acids, and are very especially

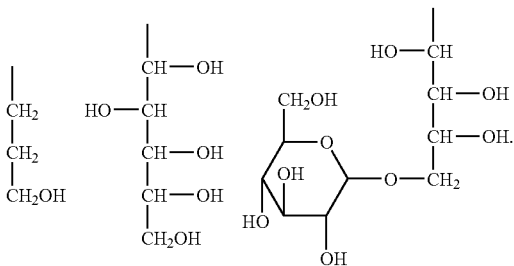

Furthermore, $R^2$ is preferably:

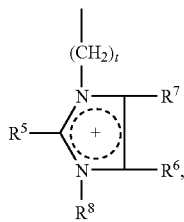

in which t and $R^5$ to $R^8$ are as defined above,

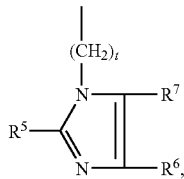

in which t and $R^5$ to $R^7$ are as defined above, and

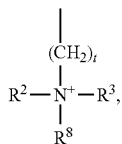

in which t and $R^2$, $R^3$ and $R^8$ are as defined above.

$V^1$ is preferably
—$R^9$—, in which $R^9$ is a divalent, saturated or mono- or polyunsaturated, straight-chain or branched hydrocarbon radical having two to 25 carbon atoms,
—$(CH_2)_u$—$R^{10}$—$(CH_2)_u$—, in which $R^{10}$ is an aromatic group,
—$[CH_2CH_2O]_q$—$[CH_2CH(CH_3)O]_r$—$CH_2CH_2$—,
—$CH(CH_3)CH_2O[CH_2CH_2O]_q$—$[CH_2CH(CH_3)O]_r$—$CH_2CH(CH_3)$—
—$CH_2CH(OH)CH_2$—,
—$CH_2CH(OH)(CH_2)_2CH(OH)CH_2$—,
—$CH_2CH(OH)CH_2OCH_2CH(OH)CH_2OCH_2CH(OH)CH_2$— and
—$CH_2CH(OH)CH_2O$—$[CH_2CH_2O]_q$—$[CH_2CH(CH_3)O]_r$—$CH_2CH(OH)CH_2$— in which
u is from 1 to 3,
q and r are from 0 to 200, preferably from 0 to 100, more preferably from 0 to 70, and with particular preference 0 to 40, and
q+r>0.

Preferred variants of $V^1$ are
alkylene, alkenylene, alkynylene and aryl units, especially those of the structures
—$[CH_2]_o$—
where o=2 to 6,

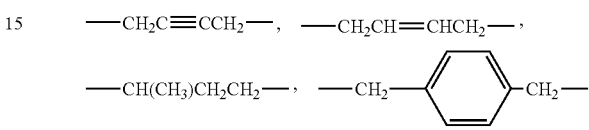

polyalkylene oxide units, especially those of the structures
—$[CH_2CH_2O]_q$—$[CH_2CH(CH_3)O]_r$—$CH_2CH_2$—,
—$CH(CH_3)CH_2O[CH_2CH_2O]_q$—$[CH_2CH(CH_3)O]_r$—$CH_2CH(CH_3)$— with
mono-, di- or polyhydroxy-functional units, especially those of the structures
—$CH_2CH(OH)CH_2$—, —$CH_2CH(OH)(CH_2)_2CH(OH)CH_2$—,
—$CH_2CH(OH)CH_2OCH_2CH(OH)CH_2OCH_2CH(OH)CH_2$—,
—$CH_2CH(OH)CH_2O$—$[CH_2CH_2O]_q[CH_2CH(CH_3)O]_r$—$CH_2CH(OH)CH_2$— with
q=0 to 200,
r=0 to 200

Preferably q=1 to 50, in particular 2 to 50, especially 1 to 20, very especially 1 to 10, and also 1 or 2, r=0 to 100, in particular 0 to 50, especially 0 to 20, very especially 0 to 10, and also 0 or 1 or 2.

The invention further provides a process for preparing the linear polysiloxanes of the invention, in which a) at least one amine compound selected from a diamine compound and/or a primary or secondary monoamine compound is reacted with at least two difunctional organic compounds capable of reacting with the amino functions of the amine compound, the molar ratio of the organic compounds being chosen so as to meet the condition $V^2/V^1 \neq 1$, b) at least two moles of an amine compound selected from a diamine compound and/or a primary or secondary monoamine compound are reacted with one mole of a difunctional organic compound capable of reacting with the amino functions of the amine compound, to form a diamine compound (monomer), which is subsequently reacted with at least one amine compound selected from a diamine compound and/or a primary or secondary monoamine compound and with at least one further difunctional organic compound capable of reacting with the amino functions of the amine compounds, c) an amine compound selected from a diamine compound and/or a primary or secondary monoamine compound is reacted with a difunctional organic compound capable of reacting with the amino functions of the amine compounds, to form a diamine compound (amino-terminated oligomer), which is subsequently reacted with at least one difunctional organic compound capable of reacting with the amino functions of the diamine compounds, d) an amine compound selected from a diamine compound and/or a primary or secondary monoamine compound is reacted with a difunctional organic compound capable of reacting with the amino functions of the amine compound, to form a difunctional compound capable of reacting with amino functions (difunctional oligomer), which is subsequently reacted with at least one amine compound selected from a diamine compound and/or a primary or secondary monoamine compound and with at least one further compound capable of reacting with amino functions, it being possible if desired to add monofunctional, preferably tertiary, monoamines or suitable monoamines not capable of chain propagation, and/or monofunctional compounds capable of reacting with amino functions, as chain terminators, and the stoichiometry of the amino functions and the functional groups capable of reacting with amino functions always being approximately 1:1 in the last stage of the reaction, and it being possible for any amino functions present to be protonated, alkylated or quaternized.

Variant a), in which at least one diamine compound selected from a diamine compound and/or primary or secondary monoamine compound is reacted with at least two difunctional organic compounds capable of reacting with the amino functions of the amine compound, the molar ratio of the organic compounds being chosen so as to meet the condition $V^2/V^1 \neq 1$, can accordingly be depicted schematically, for example, as follows:

-[N-N]-+-[V$^1$]-+-[V$^2$]-→-[Q-(V$^1$,V$^2$)]- or

-[N]-+-[V$^1$]-+-[V$^2$]-→-[Q-(V$^1$,V$^2$)]- where -[N-N]- can include a cyclic diamine corresponding to the definition of Q or a V$^1$-containing diamine -[N-V$^1$-N]- or a V$^2$-containing diamine -[N-V$^2$-N]-, such as, in particular, -[N-V$^2$*-Z$^2$-V$^2$*-N]-, the latter giving rise in each case to two Q units and/or one V$^1$ and/or two V$^2$ units, where -[V$^1$]- and -[V$^2$] are intended to denote monomers corresponding to the repeating units V$^1$ and V$^2$, and -[N]- denotes a primary or secondary monoamine suitable for chain propagation.

In this case at least one higher polyalkylated amine unit or quaternary ammonium unit Q is formed from the -[N-N]- and/or -[N]- units, it being possible for the secondary or tertiary amino functions formed during the polymerization to be protonated or quaternized in a separate step after the polymerization where appropriate. Preference is given to the formation of quaternary ammonium units.

Preferred examples of -[N-N]- are as described in more detail below: piperazine and imidazole; preferred diamine units -[N-V$^1$-N]- include, for example: polymethylenediamines, such as tetramethyl-hexamethylenediamine, α,ω-diamino-terminated polyethers, such as Jeffamines, for example, etc.

Preferred diamine units -[N-V$^{2*}$-Z$^2$-V$^{2*}$-N]- include, for example, reaction products of α,ω-dihydropolydialkylsiloxanes with allylamines.

Preferred examples of -[N]- are as described in more detail below, e.g., dimethylamine.

The use of diamines -[N-N]- is preferred per se.

Preferred -[V$^1$]- monomers include, for example, epichlorohydrin, bisepoxides or bisacrylates. It is also possible with preference to react mixtures of the stated -[V$^1$]- monomers, such as mixtures of epichlorohydrin, bis-chloroalkyl esters or bisepoxides, for example.

Preferred -[V$^2$]- monomers and monomers of formula -[V$^{2*}$-Z$^2$-V$^{2*}$]-, in which Z$^2$ is as defined above and -[V$^{2*}$] represents a functionalized group corresponding to the repeating unit V$^{2*}$. Preferred -[V$^2$]- monomers for forming the V$^2$ repeating units are, in particular, α,ω-diepoxy-terminated polydialkylsiloxanes.

Variant b) can be carried out both with diamines, -[N-N]-, and with suitable monoamines -[N]-, and can be represented diagrammatically, for example, as follows:

Variant b1)
Step 1): 2-[N-N]-+-[V$^2$]- or -[V$^1$]-→-[N-N-V$^1$-N-N]- or -[N-N-V$^2$-N-N]-
Step 2.1): -[N-N-V$^2$-N-N]-+-[V$^1$]-+-[N-N]-→,
Step 2.2): -[N-N-V$^1$-N-N]-+-[V$^2$]-+-[N-N]-→, the stoichiometry being chosen so as to meet the condition $V^2/V^1 < 1:3$.

With respect to the monomer units -[N-N]-, -[V$^1$]- and -[V$^2$]- used with preference, the remarks made with respect to step a) apply.

Variant b2)
Step 1): 2-[N]-+-[V$^2$]- or -[V$^1$]-→-[N-V$^1$-N]- or -[N-V$^2$-N]-
Step 2.1): -[N-V$^2$-N]-+-[V$^1$]-+-[N]-→,
Step 2.2): -[N-V$^1$-N]-+-[V$^2$]-+-[N]-→, it being possible to carry out this variant, as mentioned above, only with primary or secondary monoamines, and where with respect to the monomer units -[N]-, -[V$^1$]- and -[V$^2$]- used with preference, the remarks made with respect to step a) apply.

Variant c) can be depicted diagrammatically, for example, as follows:

Variant c1)
Step 1): -[N-N]-+-[V$^1$]-→-[N-N-(V$^1$-N-N)$_x$]-
Step 2): -[N-N-(V$^1$-N-N)$_x$]-+-[V$^2$]-→ where with respect to the monomer units -[N-N]-, -[V$^1$]- and -[V$^2$]- used with preference, the remarks made with respect to step a) apply.

Variant c2)
Step 1): -[N]-+-[V$^1$]-→-[N-(V$^1$-N)$_x$]-
Step 2): -[N-(V$^1$-N)$_x$]-+-[V$^2$]-→ where with respect to the monomer units -[N]-, -[V$^1$]- and [V$^2$]- used with preference, the remarks made with respect to step a) apply.

Variant d) can be depicted diagrammatically, for example, as follows:

Variant d1)
Step 1): -[V$^1$]-+-[N-N]-→-[V$^1$-(N-N-V$^1$)$_x$]-
Step 2): -[V$^1$-(N-N-V$^1$)$_x$]-+-[V$^2$]-+-[N]- or -[N-N]-→ where with respect to the monomer units -[N-N]-, -[V$^1$]- and [V$^2$]- used with preference, the remarks made with respect to step a) apply.

Variant d2)
Step 1): -[V$^1$]-+-[N]-→-[V$^1$-(N-V$^1$)$_x$]-
Step 2): -[V$^1$-(N-V$^1$)$_x$]-+-[V$^2$]-+-[N]- or -[N-N]-→ where with respect to the monomer units -[N]-, -[V$^1$]- and -[V$^2$]- used with preference, the remarks made with respect to step a) apply.

For all of the variants depicted diagrammatically above it is the case that it is also possible to use mixtures of monoamines -[N]- and diamines -[N-N]-.

With particular preference the functional groups of the difunctional compounds capable of reacting with amino functions are selected from the group consisting of epoxy groups and haloalkyl groups.

A preferred starting point for the syntheses of the linear polysiloxane copolymers of the invention are α,ω Si—H functionalized siloxanes of the general structure

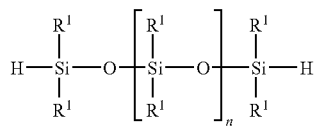

where $R^1$ is as defined above and n, in accordance with the desired repeating unit, $V^1$ or $V^2$, is $n_2$ or $n_1$, which are defined as above. Where they are not available commercially, these siloxanes can be prepared by known methods, e.g., by equilibration (Silicones, Chemie und Technologie, Vulkan-Verlag, Essen 1989, pp. 82-4).

The initial introduction of the structural elements $V^{2*}$ and Q can take place, for example, in two ways.

On the one hand it is possible first to attach unsaturated structures carrying tertiary amino functions, such as N,N-dimethylallylamine, for example, directly to the siloxane in α,ω position by hydrosilylation. This operation is general knowledge. (B. Marciniec, Comprehensive Handbook on Hydrosilylation, Pergamon Press, Oxford 1992, pp. 122-4).

On the other hand it is preferred first, by hydrosilylation, to generate reactive α,ω-functionalized intermediates, which can subsequently be converted into α,ω-ditertiary amino structures or, directly, into the quaternary ammonium structures of the invention. Suitable starting materials for generating reactive intermediates are, for example, halogenated alkenes or alkynes, especially allyl chloride, allyl bromide, chloropropyne and chlorobutyne, unsaturated halocarboxylic esters, especially allyl chloroacetate, propargyl chloroacetate, allyl 3-chloropropionate and propargyl 3-chloropropionate, and epoxy-functional alkenes, such as vinylcyclohexene oxide and allyl glycidyl ether, for example. The general procedure of hydrosilylations with representatives of the aforementioned groups of substance is likewise known (B. Marciniec, Comprehensive Handbook on Hydrosilylation, Pergamon Press, Oxford 1992, pp. 116-21, 127-30, 134-7, 151-5).

In a subsequent step the reactive intermediates can then be reacted with compounds which carry secondary amino functions. Suitable representatives are N,N-dialkyl-amines, examples being dimethylamine, diethylamine, dibutylamine, diethanolamnine and N-methylglucamine, cyclic secondary amines, examples being morpholine and piperidine, amino amides which carry secondary amino functions, examples being the reaction products of diethylenetriamine or dipropylenetriamine with lactones, such as γ-butyrolactone, glucono-δ-lactone and glucopyranosylarabolactone (DE-A 4318536, examples 11a, 12a, 13a), or secondary-tertiary diamines, such as N-methylpiperazine, for example. It is especially preferred to utilize corresponding imidazole derivatives or pyrazole derivatives, especially imidazole and pyrazole, for introducing tertiary amino functions.

Particularly suitable partners for the epoxide derivatives used with preference in one embodiment are the stated secondary-tertiary diamines, and also imidazole and pyrazole. In this way the alkylations can be directed regioselectively and without additional effort at the nitrogen atoms which carry hydrogen atoms.

In order to ensure quantitative conversion of the reactive moieties into tertiary amino structures, the amines are used in a ratio of 1≦Σ secondary amino groups: reactive groups≦10, preferably 1 to 3, especially 1 to 2, very especially 1. Any amine excesses must be removed.

The attachment of the above-described α,ω-ditertiary aminosiloxanes to monomer units -[$V^1$]- corresponding to $V^1$, or to a prepolymer unit -[$V^1$-(Q-$V^1$)$_x$]-, leads to the formation of higher polyalkylated amine units and/or quaternary ammonium units, and can again take place in two advantageous ways.

On the one hand it is preferred separately to produce a strongly hydrophilic, polyquaternary, difunctional precondensate -[$V^1$-(Q-$V^1$)$_x$]-, which at a suitable point in time is united with the α,ω-ditertiary aminosiloxanes and reacts to give the polyquaternary siloxane copolymer.

The preparation of highly charged difunctional prepolymers differing in chain length -[$V^1$-(Q-$V^1$)$_x$]- is described by way of example in WO 99/14300 (examples 1 to 7, table 11). In dependence on the molar ratio of $V^1$ and the parent amine of Q it is possible to produce either a prepolymer terminated by amino groups or a prepolymer terminated by other reactive groups (e.g., epoxy and/or haloalkyl groups).

For the case of the attachment of a prepolymer terminated by amino groups -[N-($V^1$-N)$_x$]- to the amine function of an α,ω-ditertiary aminosiloxanes structure it is possible, for example, to use an alkylating and/or quaternizing difunctional monomer -[$V^1$]-, corresponding to the repeating unit $V^1$ and selected, for example, from bisepoxides, epichlorohydin and bishaloalkyl compounds. In this context there is no need to mention that different groups $V^1$ may result in the prepolymer and in the connecting link between prepolymer and α,ω-ditertiary aminosiloxane structure.

For the case of a prepolymer terminated by reactive groups, such as -[$V^1$-(Q-$V^1$)$_x$]-, a direct attachment to the amine function of the α,ω-ditertiary aminosiloxane structure may take place without further linkers, since an excess of the component that produces $V^1$ has already been used during prepolymer synthesis.

As an alternative to the separate preparation of a precondensate -[$V^1$-(Q-$V^1$)$_x$]-, highly charged blocks can be built up in parallel for incorporation into the copolymer. This means that the α,ω-ditertiary aminosiloxane is introduced and reacted together with the starting components for the construction of -[$V^1$-(Q-$V^1$)$_x$]-, i.e., for example, -[$V^1$]- and mono- and diamines of the abovementioned definition -[N]- and/or -[N-N-]-.

Finally it is possible for the α,ω-ditertiary aminosiloxane with long-chain siloxane unit $Z^2$ or short-chain siloxane unit $Z^1$, and/or the α,ω-difunctional siloxane -[$V^{2*}$-$Z^2$-$V^{2*}$]- or -[$V^1$]-, to be metered in stages over a period of time into the initial charge of the components for constructing -[V¹-(Q-V¹)$_x$]-, or else, conversely, for these components to be added in stages to the α,ω-ditertiary aminosiloxane and/or α,ω-difunctional siloxane.

The preliminary preparation of prepolymers terminated by amino groups, such as -[N-(V¹-N)$_x$]-, for example, opens up the possibility of performing the copolymer formation directly with suitable reactive intermediates, such as epoxy derivatives, for example.

It is likewise preferred to include the reactive intermediates and the starting components for the construction of -[V¹-(Q-V¹)$_x$]- together in the initial charge and then to bring them to reaction, finally it is possible to meter the reactive intermediates into the initial charge of the components for constructing -[V¹-(Q-V¹)$_x$]- in stages over a period of time or else, conversely, to add these components in stages to the reactive intermediate.

Irrespective of the choice of one of the above-described reaction pathways, and of the closely related question of whether amino units first terminate the siloxane or else terminate the prepolymer, the overall stoichiometry is chosen such that the sum of the amino functions to the groups reactive with them amounts to approximately 1:1.

In the context of the invention it is possible to deviate from this preferred overall stoichiometry. In that case, however, products are obtained which no longer have the envisaged length of the highly charged, hydrophilic block -[V¹-(Q-V¹)$_x$]- and which additionally leave behind an excess of an unreacted starting component.

As well as the above-treated overall stoichiometry of the reaction, the choice of the component(s) forming the repeating unit V¹ is of great importance for the pattern of properties of the products.

The introduction of alkylene, alkenylene, alkynylene and aryl units takes place preferably starting from the corresponding halides, especially chlorides and bromides. Exemplary representatives are 1,6-dichlorohexane, 1,4-dichlorobut(2-)ene, 1,4-dichlorobut(2-)yne and 1,4-bis(chloromethyl)benzene.

Polyalkylene oxide units may likewise be introduced by the α,ω-dihalogen compounds. They are obtainable from the oligomeric and polymeric alkylene oxides of the general composition

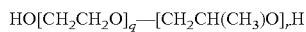

where q and r are as defined above, by, for example, chlorinating the hydroxyl groups with SOCl$_2$ (Organikum, Organisch-chemisches Grundpraktikum, 17th edition, VEB Deutscher Verlag der Wissenschaften, Berlin 1988, pp. 189-90). Mono-, di- or polyhydroxy-functional units as group V¹ can be introduced starting from epoxide derivatives.

Commercial examples are 1-chloro-2,3-epoxypropane, glycerol 1,3-bisglycidyl ether and diethylene glycol diglycidyl ether and neopentyl glycol diglycidyl ether.

Where not available commercially, the desired diepoxides can be synthesized, for example, by reacting the corresponding diols with 1-chloro-2,3-epoxypropane under alkaline conditions.

It is within the bounds of the invention to introduce siloxane chains Z¹ into the structure of V¹. This gives rise to the possibility, among others, of using siloxane chains of different length to construct the overall molecule. A preferred variant is to incorporate into V¹ siloxane chains Z¹ of the chain-length range n$_2$=0 to 19, preferably 0 to 15, more preferably 0 to 10, especially 0 to 5, more especially 0. Examples of suitable starting materials for the incorporation are the corresponding α,ω-diepoxides.

In the case of the reaction of epoxides with primary or secondary amines it should be borne in mind that for alkylations of tertiary amino groups it is necessary to add one mole of H+ per mole of epoxide/tertiary amine.

The choice of suitable amines as starting components for the formation of Q in the repeating unit -[V¹-(Q-V¹)$_x$]- likewise determines to a high degree the molecular structure. The use of ditertiary amines (corresponding to -[N-N]-), for example, N,N,N',N'-tetramethylethylenediamine, N,N,N',N'-tetramethyltetramethylenediamine, N,N,N',N'-tetramethylhexamethylenediamine and N,N'-dimethylpiperazine, leads to products in which each nitrogen atom of the repeating unit is quaternized.

The use of secondary-tertiary diamines, such as N-methylpiperazine, for example, opens up a pathway to repeating units -[V¹-(Q-V¹)$_x$]-, in which tertiary and quaternary amine and ammonium structures, respectively, are present in the ratio of 1:1. Partial or complete subsequent quaternization of remaining tertiary amino structures constitutes one preferred variant for setting a desired high density of quaternary ammonium groups. The corresponding aromatic amines imidazole and pyrazole, respectively, lead to products having a delocalized charge.

When primary-tertiary diamines are used, N,N-dimethylpropylenediamine and 1-(3-aminopropyl)imidazole, for example, especially in combination with diepoxides, it is possible to construct comblike structures, for which the degree of quaternization during a final alkylation is selectable. In principle it is also possible for the alkylations to be set to degrees of quaternization of, on average; less than one quaternary ammonium group per repeating unit -[V¹-(Q-V¹)$_x$]-. It is, however, preferred to quaternize at least one nitrogen atom per repeating unit.

Starting from disecondary amines, such as piperazine, N,N'-bis(2-hydroxyethyl)-hexamethylenediamine and N,N'-bis(2-hydroxypropyl)hexamethylenediamine, for example, it is in principle also possible to synthesize repeating units -[V¹-(Q-V¹)$_x$]- having an average content of less than one quaternary ammonium group. In this case the disecondary amines first yield polytertiarily amino-modified siloxane copolymers or else prepolymers, which in a final reaction can be fully or partly quaternized to -[V¹-(Q-V¹)$_x$]-. In this variant as well, however, it is preferred to quaternize at least one nitrogen atom per repeating unit.

Suitable quaternizing agents include the groups of substance that are general knowledge, such as alkyl halides, halocarboxylic esters, epoxide derivatives in the presence of H+, and dialkyl sulfates, especially dimethyl sulfate.

The preparation of disecondary amines that are not available commercially takes place in one preferred embodiment starting from the corresponding diprimary amines, such as hexamethylenediamine, for example, by alkylation with epoxides, such as ethylene oxide, propylene oxide or isopropyl glycidyl ether, for example, utilizing the different reaction rates of primary and secondary amines.

It has already been established that within the bounds of the invention the possibility exists of introducing siloxane chains $Z^1$ into the structure of $V^1$. Suitable starting materials designated were, by way of example, the reactive intermediates α,ω-diepoxides.

Suitable neutralizing anions $A^-$ for the positive charges that result from the ammonium groups include preferably the ions that are formed during the quaternization, such as halide ions, especially chloride and bromide, alkyl sulfates, especially methosulfate, carboxylates, especially acetate, propionate, octanoate, decanoate, dodecanoate, tetradecanoate, hexadecanoate, octadecanoate and oleate, and sulfonates, especially toluenesulfonate. By means of ion exchange, however, it is also possible to introduce other anions. Examples that may be mentioned include organic anions, such as polyethercarboxylates and polyethersulfates.

The quaternization reactions are performed preferably in water, polar organic solvents or mixtures of both stated components. Suitability is possessed for example by alcohols, especially methanol, ethanol, isopropanol and n-butanol, glycols, such as ethylene glycol, diethylene glycol, triethylene glycol, the methyl, ethyl and butyl ethers of said glycols, 1,2-propylene glycol and 1,3-propylene glycol, ketones, such as acetone and methyl ethyl ketone, esters, such as ethyl acetate, butyl acetate and 2-ethylhexyl acetate, ethers, such as tetrahydrofuran and nitro compounds, such as nitromethane. The choice of solvent is governed essentially by the solubility of the reactants, by the target reaction temperature and by the presence of any reactivity that disrupts the reaction.

The reactions are performed in the range from 20° C. to 130° C., preferably 40° C. to 100° C.

In order to avoid the formation of gel-like linear polyorganosiloxane polymers that are not fully soluble, it is advantageous to place an upper limit on the molar weight. A limit on the molecular weight is placed by means of the end stopping that arises during the reaction between epoxides and any alcohol or water that may be present in the reaction system, or, alternatively, through the additional use of tertiary amines, such as trialkylamines or monofunctional amino-reactive compounds.

In other words, the linear polyorganosiloxane polymers may contain not only the terminal groups that result naturally from the reaction of the monomeric starting materials but also from monofunctional chain terminators, such as trialkylamines, etc., and, for example, resultant ammonium, amino, ether or hydroxyl end groups.

The present invention further provides for the use of the linear polyorganosiloxane polymers of the invention and, respectively, of the linear polyorganosiloxane polymers obtained by the process of the invention in cosmetic formulations, in laundry detergents or for surface-treating substrates.

The linear polyorganosiloxane polymers of the invention, which combine the softening properties of siloxane structures with the tendency of quaternary ammonium groups toward adsorption on negatively charged surfaces of solids can be used with success in cosmetic formulations for skincare and haircare, in polishes for treating and finishing hard surfaces, in formulations for drying automobiles and other hard surfaces after machine washing, for finishing textiles, textile fibers, paper, paper fibers, paper webs, including the pretreatment and finish treatment of fiber, textile and paper, finishing paper for the cosmetics and sanitary segments, especially permanent hydrophilic softeners, as separate softeners after the laundering of textiles with anionic/nonionic detergent formulations, as softeners in textile laundry formulations based on anionic/nonionic surfactants, and also as an ironing aid and as agents for preventing or reducing textile creasing. The invention further provides compositions comprising at least one of the linear polyorganosiloxane polymers of the invention together with at least one further ingredient usual for the composition, such as cosmetic compositions, laundry detergent compositions, polishes, shampoos, ironing aids and crease-free finishes.

Use of the polysiloxane derivatives of the invention in hair cosmetology applications leads to favorable effects in terms of gloss, fixing (hold), body, volume, moisture regulation, color retention, environmental protection (UV, salt water, etc.), reshapeability, antistatic properties, colorability, combability, etc. In other words, the quaternary polysiloxane compounds can be used with preference in the cosmetics and haircare formulas of WO 02-10257.

EXAMPLES

Example 1

19.38 g (0.225 mol of amino groups) of N,N,N',N'-tetramethylhexanediamine and 12.14 g (0.202 mol) of acetic acid are mixed with 30 ml of deionized water at room temperature. Added dropwise to this solution over the course of 15 minutes are 35.26 g (0.202 mol of epoxy groups) of a 50% strength solution of ethylene glycol diglycidyl ether in ethylene glycol dimethyl ether. The temperature climbs to 92° C. Within an afterreaction time of 20 minutes a gel-like mass develops. This gel mass is added to a mixture of 150 g (0.025 mol of epoxy groups) of an epoxysiloxane of the structure

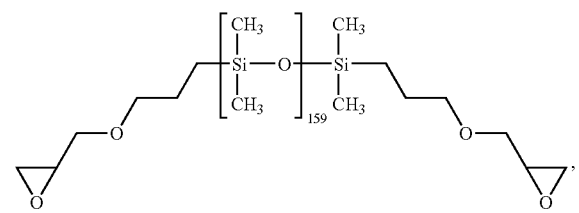

0.75 g (0.0125) of acetic acid, 2.5 g (0.0125 mol) of dodecanoic acid, 0.33 g (0.0025 mol; 45% strength aqueous solution) of trimethylamine and 50 ml of 2-propanol. Reaction takes place over 16 hours at 90° C. Subsequently all of the volatile constituents are stripped off at 20 hPa/80° C. This gives 182 g of a white, solid to waxlike material. The following formula shows the quantitative composition:

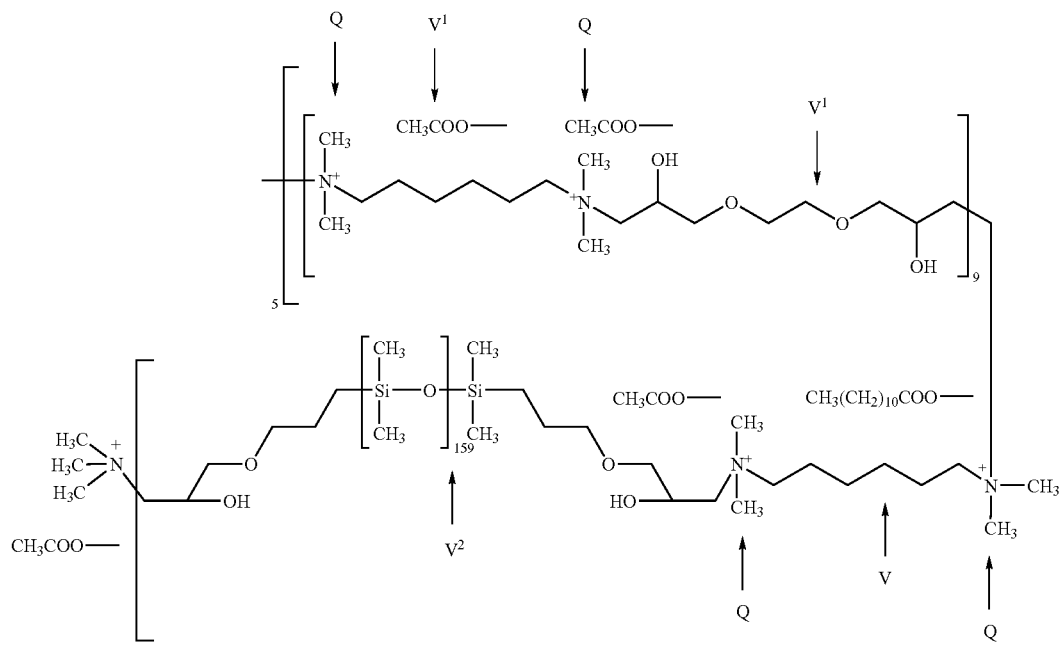

The ratio $V^2/V^1$ for this example is about 0.058.

Example 2

27.6 g (0.255 mol of epoxy groups) neopentyl diglycidyl ether and 54.8 g (0.0316 mol of epoxy groups) of a siloxane of the structure

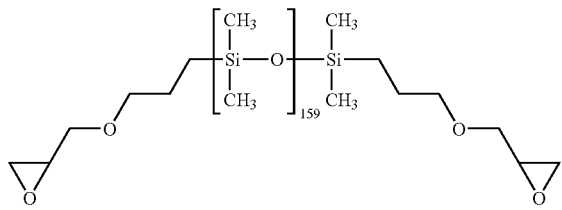

are dissolved at room temperature in 200 ml of 2-propanol. Added to this solution are 17.8 g (0.142 mol of primary amino groups) of 1-(3-aminopropyl)imidazole. The ring-opening reaction takes place at 80° C. for 8 hours. Subsequently 17.9 g (0.142 mol) of dimethyl sulfate are added and the quaternization reaction is carried out over the course of 5 hours. Residues of dimethyl sulfate are destroyed by adding 10 ml of water. After all of the constituents which boil at up to 20 hPa/60° C. have been stripped off, 97.5 g of a brown, turbid product are obtained. The following formula shows the quantitative composition:

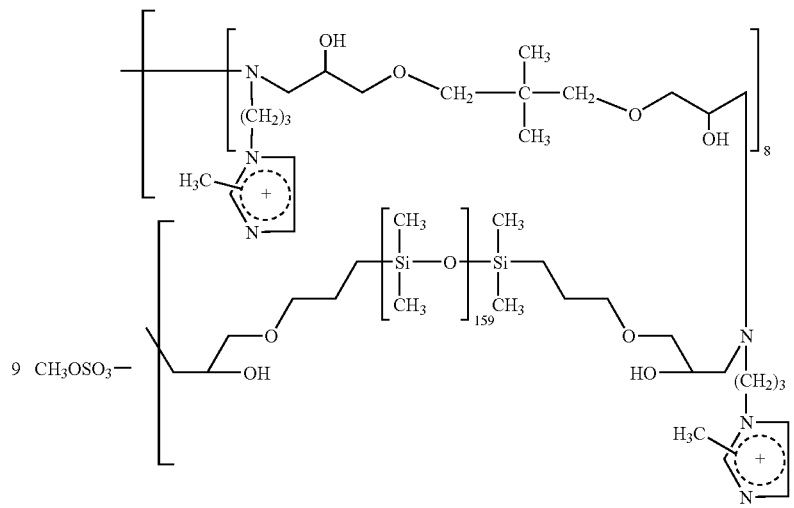

Example 3

9.67 g (0.112 mol of amino groups) N,N,N',N'-tetramethylhexanediamine, 0.17 g (0.0013 mol) of 45% strength aqueous trimethylamine solution, 11.35 g (0.056 mol) of dodecanoic acid and 3.4 g (0.056 mol) of acetic acid are mixed with 6 ml of deionized water and 124 g of 2-propanol at room temperature and the mixture is heated to 50° C. Introduced dropwise into the clear solution are 86.85 g (0.0124 mol of epoxy groups) of an epoxysiloxane of the structure

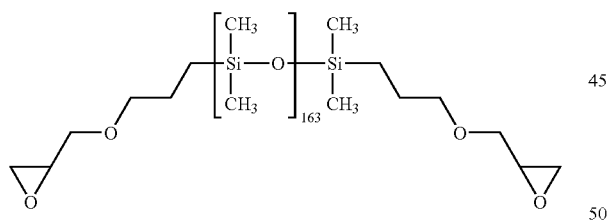

and 18.28 g (0.101 mol of epoxy groups) of an epoxysiloxane of the structure

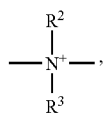

The reaction mixture is heated to 84° C. and maintained at this temperature for 14.5 hours. After 15 minutes, incipient turbidification was observed. After the end of the reaction the mixture is divided. From one half of the mixture all of the volatile constituents are stripped off at 20 hPa/80° C. This gives 54 g of a viscous, almost white mass. From the other half of the mixture the volatile constituents are removed at 20 hPa/25° C. This gives 58 g of a pale yellowish, viscous oil. The following formula shows the quantitative composition:

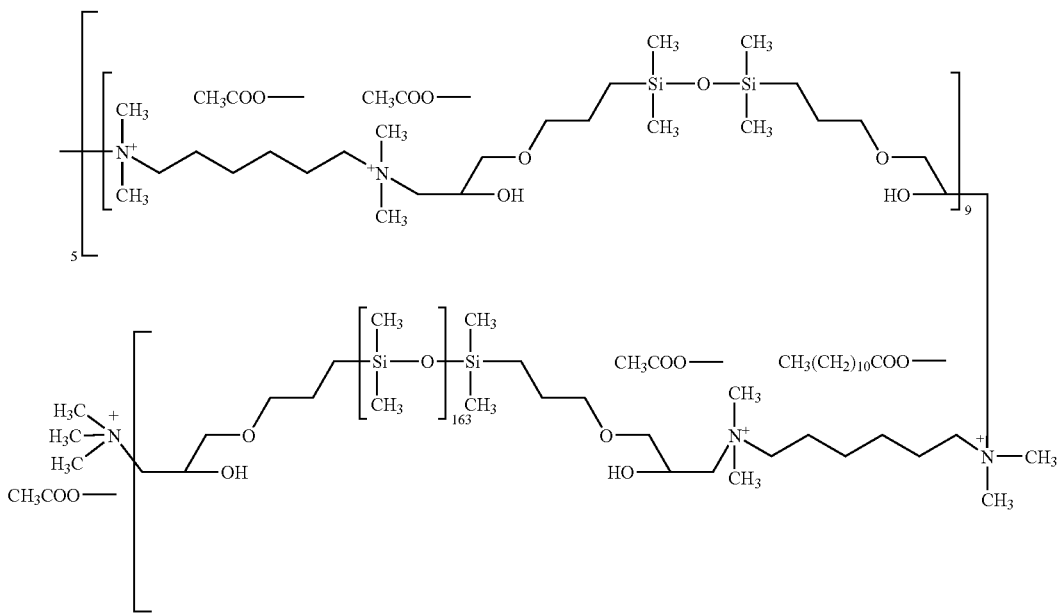

The ratio $V^2/V^1$ in this example is about 0.058.

The invention claimed is:

1. Linear polyammonium-polysiloxane copolymers containing the repeating unit $$-[Q-V-]- \quad (I)$$

in which Q is selected from the group consisting of

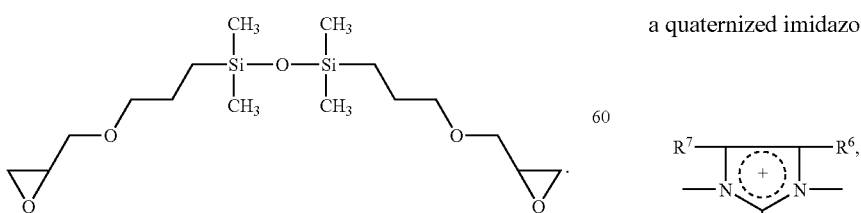

a quaternized imidazole unit of the structure

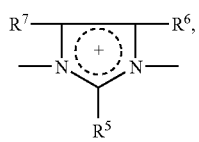

a quaternized pyrazole unit of the structure

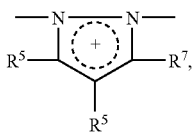

a diquaternized piperazine unit of the structure

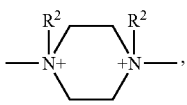

a monoquaternized piperazine unit of the structure

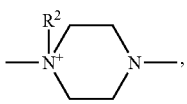

a monoquaternized piperazine unit of the structure

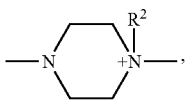

a monoquaternized unit of the structure

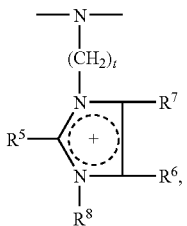

in which $R^2$ is a monovalent, straight-chain, cyclic or branched, saturated, unsaturated or aromatic hydrocarbon radical having up to 100 carbon atoms, which may contain one or more groups selected from —O—, —NH—, —C(O)— and —C(S)—, and which may if desired be substituted by one or more substituents selected from the group consisting of a hydroxyl group, an unsubstituted or substituted heterocyclic group preferably containing one or more nitrogen atoms, amino, alkylamino, dialkylamino, ammonium, polyether radicals and polyetherester radicals, and, if there are two or more groups —CONR$^2$—, they may be identical or different, $R_3$ has the definition of $R^2$, it being possible for $R^2$ and $R^3$ to be identical or different, or $R^2$ and $R^3$ together with the positively charged nitrogen atom form a five- to seven-membered heterocycle, which if desired may additionally contain one or more nitrogen, oxygen and/or sulfur atoms, $R^5$, $R^6$ and $R^7$ can be identical or different and are selected from the group consisting of hydrogen, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the type —NHR$^W$, in which R$^W$ is hydrogen, alkyl group, monohydroxyalkyl group, polyhydroxyalkyl group, acetyl group or ureido group, and pairs of adjacent radicals $R^5$, $R^6$ and $R^7$ may, with the carbon atoms bonding them to the heterocycle, form aromatic five- to seven-membered rings, and $R^8$ has the definition of $R^2$, it being possible for $R^8$ and $R^2$ to be identical or different, Q not bonding to a carbonyl carbon atom, V represents at least one group $V^1$ or at least one group $V^2$ in which $V^2$ is selected from divalent or trivalent, straight-chain, cyclic or branched, saturated, unsaturated or aromatic hydrocarbon radicals having up to 1000 carbon atoms (not including the carbon atoms of the polysiloxane radical $Z^2$, defined below) and containing, if desired, one or more groups selected from
—O—, —CONH—,
—CONR$^2$—, in which $R^2$ is as defined above,
—C(O)— and —C(S)—, and the radical $V^2$ may if desired by substituted by one or more hydroxyl groups, and the radical $V^2$ contains at least one group -$Z^2$- of the formula

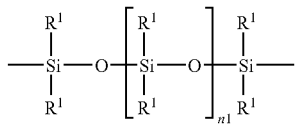

in which
$R^1$ can be identical or different and is selected from the group consisting of $C_1$ to $C_{22}$ alkyl, fluoro($C_1$-$C_{10}$)alkyl and $C_6$-$C_{10}$ aryl, and $n_1$=20 to 1000, $V^1$ is selected from divalent or trivalent, straight-chain, cyclic or branched, saturated, unsaturated or aromatic hydrocarbon radicals having up to 1000 carbon atoms, which if desired may contain one or more groups selected from
—O—, —CONH—,
—CONR$^2$—, in which $R^2$ is as defined above, it being possible for the groups $R^2$ in the groups $V^1$ and $V^2$ to be identical or different,
—C(O)—, —C(S)— and -$Z^1$-, in which -$Z^1$- is a group of the formula

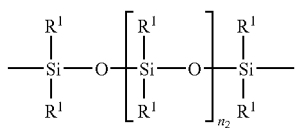

in which
$R^1$ is as defined above, it being possible for the groups $R^1$ in the groups $V^1$ and $V^2$ to be identical or different, and $n_2$=0 to 19, and the radical $V^1$ may if desired be substituted by one or more hydroxyl groups, with the provisos that the radical $V^1$ may not contain any ester group(s) —C(O)—O— and/or —O—C(O)—, and that in the stated polysiloxane copolymer the molar ratio $V^2/V^1 \neq 1$, and in which the positive charges resulting from the ammonium groups are neutralized by organic or inorganic acid anions, and the acid addition salts thereof.

2. Linear polyammonium-polysiloxane copolymers according to claim 1, in which $V^2$ is a group of the formula

-$V^{2*}$-$Z^2$-$V^{2*}$- in which $Z^2$ is as defined above and $V^{2*}$ is a divalent straight-chain cyclic or branched, saturated, unsaturated or aromatic hydrocarbon radical having up to 40 carbon atoms, which if desired may contain one or more groups selected from —O—, —CONH—, —CONR$^2$—, in which $R^2$ is as defined above, —C(O)— and —C(S)—, and the radical $V^{2*}$ may if desired be substituted by one or more hydroxyl groups.

3. Linear polyammonium-polysiloxane copolymers according to claim 1, in which the group $V^1$ is selected from divalent, straight-chain, cyclic or branched, saturated, unsaturated or aromatic hydrocarbon radicals having up to 600 carbon atoms, which may if desired contain one or more groups selected from —O—, —CONH—, —CONR$^2$—, in which $R^2$ is as defined above, —C(O)—, —C(S)— and -$Z^1$-, in which -$Z^1$- is a group of the formula

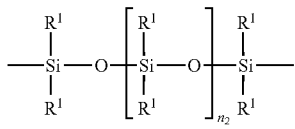

in which $R^1$ is $C_1$ to $C_3$ alkyl, fluoro($C_3$-$C_6$)alkyl or $C_6$ aryl, and $n_2$ is as defined above.

4. Linear polyammonium-polysiloxane copolymers according to claim 1, in which the molar ratio $V^2/V^1$ complies with the relationship $V^2/V^1$<1.

5. Linear polyammonium-polysiloxane copolymers according to claim 1, in which the molar ratio $V^2/V^1$ complies with the relationship 0.0005<$V^2/V^1$<0.9.

6. A process for preparing the linear polyammonium-polysiloxane copolymers according to claim 1, in which a) at least one amine compound selected from a diamine compound and/or a primary or secondary monoamine compound is reacted with at least two difunctional organic compounds capable of reacting with the amino functions of the amine compound, the molar ratio of the organic compounds being chosen so as to meet the condition $V^2/V^1 \neq 1$, b) at least two moles of an amine compound selected from a diamine compound and/or a primary or secondary monoamine compound are reacted with one mole of a difunctional organic compound capable of reacting with the amino functions of the amine compound, to form a diamine compound (monomer), which is subsequently reacted with at least one amine compound selected from a diamine compound and/or a primary or secondary monoamine compound and with at least one further difunctional organic compound capable of reacting with the amino functions of the amine compounds, c) an amine compound selected from a diamine compound and/or a primary or secondary monoamine compound is reacted with a difunctional organic compound capable of reacting with the amino functions of the amine compounds, to form a diamine compound (amino-terminated oligomer), which is subsequently reacted with at least one difunctional organic compound capable of reacting with the amino functions of the diamine compounds, or d) an amine compound selected from a diamine compound and/or a primary or secondary monoamine compound is reacted with a difunctional organic compound capable of reacting with the amino functions of the amine compound, to form a difunctional compound capable of reacting with amino functions (difunctional oligomer), which is subsequently reacted with at least one amine compound selected from a diamine compound and/or a primary or secondary monoamine compound and with at least one further compound capable of reacting with amino functions, it being possible if desired to add monofunctional, preferably tertiary, monoamines or suitable monoamines not capable of chain propagation, and/or monofunctional compounds capable of reacting with amino functions, as chain terminators, and the stoichiometry of the amino functions and the functional groups capable of reacting with amino functions always being approximately 1:1 in the last stage of the reaction, and it being possible for any amino functions present to be protonated, alkylated or quaternized.

7. The process according to claim 6, in which the functional groups of the difunctional compounds capable of reacting with amino functions are selected from the group consisting of epoxy groups and haloalkyl groups.

8. A process of applying a cosmetic comprising applying a composition including the linear polyammonium-polysiloxane copolymers according to claim 1.

9. A process of treating fibers or finishing fibers comprising applying the formulation according to claim 1 to fibers.

10. Compositions comprising at least one linear polyammonium-polysiloxane copolymer according to claim 1, together with at least one further ingredient customary for the composition.

11. A laundry detergent composition comprising the composition according to claim 10.

12. A process of washing laundry comprising applying the linear polyammonium-polysiloxane copolymer according to claim 1 to laundry.

13. A process of surface treating a substrate comprising applying the polyammonium-polysiloxane compound of claim 1 to the substrate.

14. A cosmetic composition comprising the composition according to claim 10.

* * * * *